(12) United States Patent  (10) Patent No.: US 7,937,139 B2
Horne et al.  (45) Date of Patent: May 3, 2011

(54) SYSTEMS AND METHODS OF UTILIZING ELECTRICAL READINGS IN THE DETERMINATION OF TREATMENT

(75) Inventors: Douglas S. Horne, Murray, UT (US); Phillip Dietz, Saint George, UT (US); Harold E. Swift, Lehi, UT (US); Valentine C. Krzyzaniak, Federal Way, WA (US); Jacob L. Carter, Playa Vista, CA (US); Bruce R. Shelton, Phoenix, AZ (US)

(73) Assignee: BioMeridian International, Inc., Salt Lake City, UT (US)

( * ) Notice: Subject to any disclaimer, the term of this patent is extended or adjusted under 35 U.S.C. 154(b) by 40 days.

(21) Appl. No.: 10/895,149

(22) Filed: Jul. 20, 2004

(65) Prior Publication Data

US 2006/0020223 A1  Jan. 26, 2006

(51) Int. Cl.
*A61B 5/05* (2006.01)
*A61B 5/04* (2006.01)
*A61H 39/02* (2006.01)

(52) U.S. Cl. .......................... 600/547; 600/546; 600/548

(58) Field of Classification Search .................. 600/547, 600/548, 300, 306, 546; 128/907; 607/1, 607/2, 3, 45, 58, 63
See application file for complete search history.

(56) References Cited

U.S. PATENT DOCUMENTS

| | | | |
|---|---|---|---|
| 2,684,670 A | 7/1954 | Mathison | 128/2.1 |
| 3,508,540 A | 4/1970 | Cavallari, Jr. et al. | 128/2.1 |
| 3,784,908 A | 1/1974 | Anderson | 324/62 |
| 3,894,532 A | 7/1975 | Morey | 128/2.1 |
| 3,971,366 A * | 7/1976 | Motoyama | 600/384 |
| 3,980,073 A | 9/1976 | Shaw, IV | 128/2 |
| 4,016,870 A | 4/1977 | Lock | 128/2.1 |
| 4,052,978 A | 10/1977 | Eugenio | 600/548 |
| 4,088,125 A | 5/1978 | Forgione et al. | 128/2.1 |
| 4,096,582 A | 6/1978 | Bailey et al. | 365/13 |
| 4,290,114 A * | 9/1981 | Sinay | 600/301 |
| 4,408,617 A | 10/1983 | Auguste | 128/735 |
| 4,557,271 A * | 12/1985 | Stoller et al. | 600/547 |
| 4,832,036 A | 5/1989 | Cartmell | 128/640 |
| 4,940,060 A | 7/1990 | Gu et al. | 128/735 |
| 4,947,862 A | 8/1990 | Kelly | 128/734 |
| 5,012,816 A | 5/1991 | Lederer | 128/735 |
| 5,024,236 A | 6/1991 | Shapiro | 128/735 |
| 5,205,330 A | 4/1993 | Sekine | 141/59 |
| 5,339,827 A | 8/1994 | Masopust | 128/735 |
| 5,366,379 A * | 11/1994 | Yang et al. | 434/365 |
| 5,409,011 A | 4/1995 | Alexeev et al. | 128/734 |
| 5,505,208 A * | 4/1996 | Toomim et al. | 600/546 |
| 5,935,060 A * | 8/1999 | Iliff | 600/300 |
| 5,938,593 A | 8/1999 | Ouellette | 600/300 |
| 5,961,471 A | 10/1999 | Nickson | 600/546 |
| 6,004,312 A | 12/1999 | Finneran et al. | 604/546 |
| 6,026,322 A | 2/2000 | Korenman et al. | 600/547 |
| 6,067,468 A | 5/2000 | Korenman et al. | 600/547 |
| 6,285,905 B1 | 9/2001 | Chiang et al. | 607/2 |

(Continued)

*Primary Examiner* — Jeffrey G Hoekstra
(74) *Attorney, Agent, or Firm* — Kirton & McConkie; Michael F. Krieger

(57) ABSTRACT

The present invention relates to a system for determining treatment options from at least two electrical readings. The electrical readings are conductivity measurements of a particular region on the human body. The system utilizes a correlation algorithm to determine the diagnosis which can easily be correlated with appropriate treatments. The correlation algorithm may include the analysis of multiple electrical readings in determining the diagnosis. The system may also utilize a database of clinical data to further assist in determining the diagnosis.

31 Claims, 4 Drawing Sheets

U.S. PATENT DOCUMENTS

| | | | |
|---|---|---|---|
| 6,299,586 B1 | 10/2001 | Cao | 601/134 |
| 6,306,160 B1 | 10/2001 | Nidetzky | 607/89 |
| 6,347,238 B1 | 2/2002 | Levengood et al. | 600/372 |
| 6,392,362 B1 | 5/2002 | Ito | 315/224 |
| 6,480,735 B2 | 11/2002 | Colloca et al. | 600/546 |
| 6,633,777 B2 * | 10/2003 | Szopinski | 600/547 |
| 2001/0034491 A1 | 10/2001 | Benson et al. | 600/547 |
| 2002/0151815 A1 | 10/2002 | Kawanishi et al. | 600/547 |
| 2003/0045809 A1 * | 3/2003 | Kanevsky | 600/547 |
| 2004/0087838 A1 * | 5/2004 | Galloway et al. | 600/300 |
| 2004/0133121 A1 * | 7/2004 | Ohkura | 600/547 |

* cited by examiner

| | Reading 1 | Reading 2 | ...Reading x | Symptom 1 | Symptom 2 | ...Symptom x | Diagnosis |
|---|---|---|---|---|---|---|---|
| Patient 1 | 76 | 40 | 75 | Runny nose | Body Aches | Painful joints | Influenza |
| Patient 2 | 35 | 38 | 75 | shortness of breath | chest pain | discoid rash | Lupus Erythematosus |
| ...Patient x | 78 | 69 | 52 | Fever above 40 C | Severe muscle pain | Swelling of tissues | Trichinosis |

Figure 4

SYSTEMS AND METHODS OF UTILIZING ELECTRICAL READINGS IN THE DETERMINATION OF TREATMENT

BACKGROUND OF THE INVENTION

1. Field of the Invention

The present invention relates to treatment and diagnosis methods. More particularly, the present invention relates to a method of determining treatment from electrical readings.

2. Background and Related Art

Traditional medical science has long recognized certain electrical characteristics of humans and other living organisms. For example, the traditional medical community has recognized electrical potentials generated by the human body in such forms as brain waves, detected by electro-encephalographs (EEG), electrical impulses resulting from muscular heart activity, as detected by electrocardiograms (EKG), and other electrical potentials measurable at other areas of the human body. While the levels of electrical activity at sites on the human body are relatively small, such signals are nonetheless measurable and consistent across the species.

In addition to measurable currents, the human body and other mammalian organisms exhibit specific locations where a resistance value and, inversely, a conductance value are relatively predictable for healthy individuals. These locations, known as anatomical dermal conductance points, exhibit unique resistance values. Interestingly, such locations exhibit a resistive reading of approximately 100,000 ohms and coincide with the acupuncture points defined anciently by the Chinese.

Ancient Chinese medical practitioners treated many unfavorable health conditions by inserting thin needles into the body at specific points to pierce peripheral nerves, a technique commonly known as acupuncture. Acupressure is a gentle, noninvasive form of the ancient Chinese practice of acupuncture that implements thumb or finger pressure or electrical stimulation at these same points, also known as acupressure points, to provide similar results.

The representative acupressure points and their relationship with organs and life systems of the human body have been characterized into more than 800 points that are organized into approximately 12 basic meridians that run along each side of the body. Each pair of meridians corresponds to a specific organ or function such as stomach, liver, spleen/pancreas and lung. Acupressure points are named for the meridian they lie on, and each is given a number according to where along the meridian it falls. For example, Spleen 6 is the sixth point on the Spleen meridian. The measurable attributes of each acupressure point reflect the energetic condition of the inner organ or other functions of the human body corresponding to such point.

As introduced above, the resistance value of healthy tissue measured at an acupressure point is generally in the range of about 100,000 ohms. When conditions arise affecting higher electrical readings, perhaps from inflammation or infection, the measured resistance value becomes less than 100,000 ohms. Likewise when conditions arise affecting lower electrical readings, perhaps from tissue fatigue or a degenerative state, conductivity is reduced, causing the resistance value to be higher.

Systems have been implemented to measure a resistance, voltage, and/or current values at acupressure points located on a meridian and to present the values to a clinician for use in assessing a condition. Unfortunately, these existing systems fail to suggest appropriate treatments in response to the readings. Therefore, the readings must be interpreted by a practitioner based on his/her education and experience. This type of system invariably limits the amount of information that can be obtained from the readings because it is tied to the specific knowledge of the practitioner. It is therefore desirable for a system to automatically suggest treatments from the readings based on as much data as possible.

SUMMARY OF THE INVENTION

The present invention relates to a system for determining treatment options from at least two electrical readings. The electrical readings are conductivity measurements of a particular region on the human body. The system utilizes a correlation algorithm to determine the diagnosis which can easily be correlated with appropriate treatments. The correlation algorithm may include the analysis of multiple electrical readings in determining the diagnosis. The system may also utilize a database of clinical data to further assist in determining the diagnosis.

In one embodiment, the system includes measuring electrical readings, determining possible diagnoses, and determining a treatment. The measurement of electrical readings includes the measurement of electrical impedance from acupressure points to another location on the human body. The diagnosis is determined by further obtaining symptom information about the patient, correlating the symptom information with the electrical readings, and determining the diagnosis based on the correlated information. The diagnosis is then used to formulate an appropriate treatment for the patient. The treatment is determined by comparing the diagnosis to known treatments.

While the methods and processes of the present invention have proven to be particularly useful in the area of health and healing, those skilled in the art can appreciate that the methods and processes can be used in a variety of different applications and in a variety of different areas of manufacture.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which:

FIG. 4 illustrates one embodiment of a clinical database for use with the present invention.

DETAILED DESCRIPTION OF THE INVENTION

The present invention relates to a system for determining treatment options from at least two electrical readings. The electrical readings are conductivity measurements of a particular region on the human body. The system utilizes a correlation algorithm to determine the diagnosis which can easily be correlated with appropriate treatments. The correlation algorithm may include the analysis of multiple electrical readings in determining the diagnosis. The system may also utilize a database of clinical data to further assist in determining the diagnosis. While embodiments of the present invention are directed at medical and homeopathic applications, it will be appreciated that the teachings of the present invention are applicable to other fields.

Figure 1:
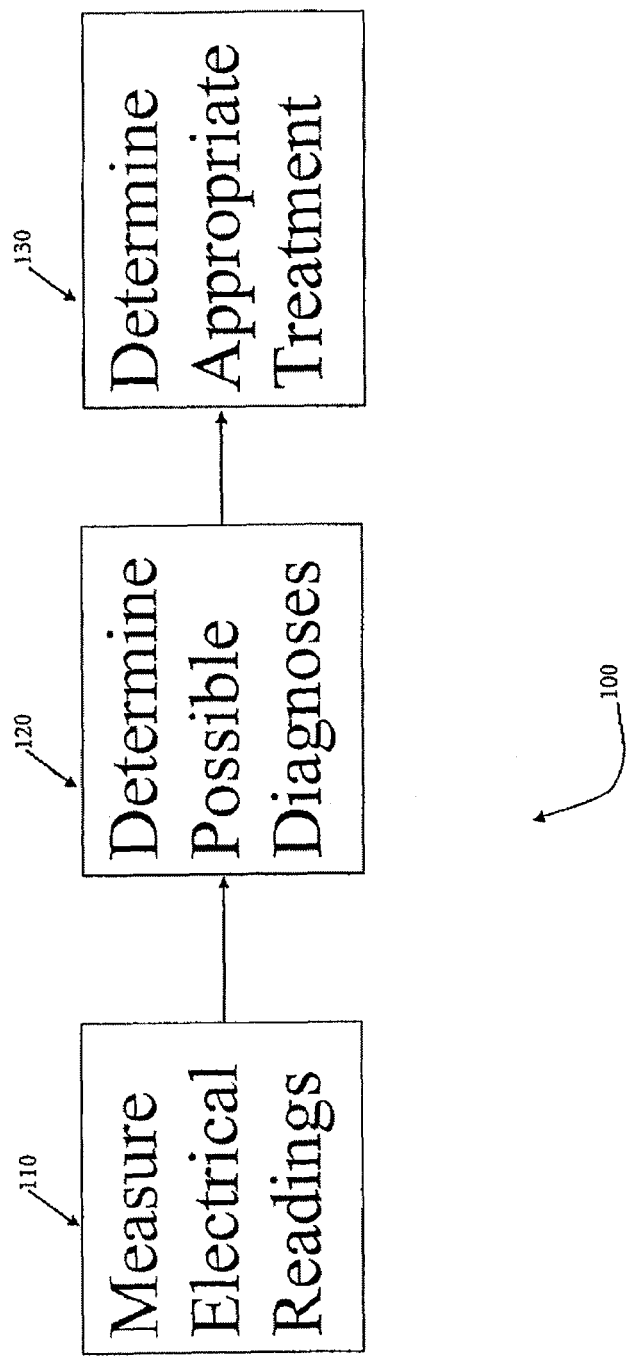
FIG. 1 illustrates a flow chart of one embodiment of the present invention.

Reference is initially made to FIG. 1, which illustrates a flow chart of one embodiment of the present invention, designated generally at 100. The treatment system 100 of the present invention includes three general acts: measuring electrical readings 110, determining diagnosis 120, and determining appropriate treatment 130. Various other steps or acts may be included in this system and remain consistent with the present invention.

One embodiment of measuring electrical readings, act 110, involves measuring the electrical impedance of the patient through a particular path. Various devices known in the field are capable of measuring these readings including but not limited to Galvanic Skin Response devices. For example, the impedance from a patient's left hand through their torso and back out their right hand can be measured by placing a ground in the patient's right hand and an electrical measurement device on their left hand. Impedance is a measurement that includes the resistance through the particular path. It is generally known in the art that when the impedance of a particular region drops below or rises above a certain threshold, it is an indicator of a problem. Alternatively, the measurement of electrical readings 110 could involve the analysis of other electrical properties including but not limited to the square wave response, rectifying response, frequency filtration response, etc.

The act of determining the diagnosis 120 can be accomplished in various ways; two of which are described in more detail with reference to FIGS. 2 and 3. Because of FDA and other medical regulations, the system may or may not display the determined diagnosis. The word diagnosis is used in the broadest sense to include medical disorders, homeopathic ailments, chiropractic conditions, etc. The determination of a diagnosis generally involves analyzing the electrical readings individually or in combination. All prior art devices rely on individual electrical readings to determine a patient's diagnosis. The present invention includes the ability to combine readings to more accurately diagnose a particular ailment.

One embodiment of determining the appropriate treatment, act 130, involves assigning a treatment based on known treatments for the particular diagnosis determined in act 120. Alternatively, the determination of treatments could include the utilization of one or more of the following: known homeopathic treatments, known prescription treatments, known chiropractic treatments, known herbal treatments or known food treatments. Likewise, the system 100 could include the ability to view one or all of these types of suggested treatments depending on a set of defined parameters.

Figure 2:
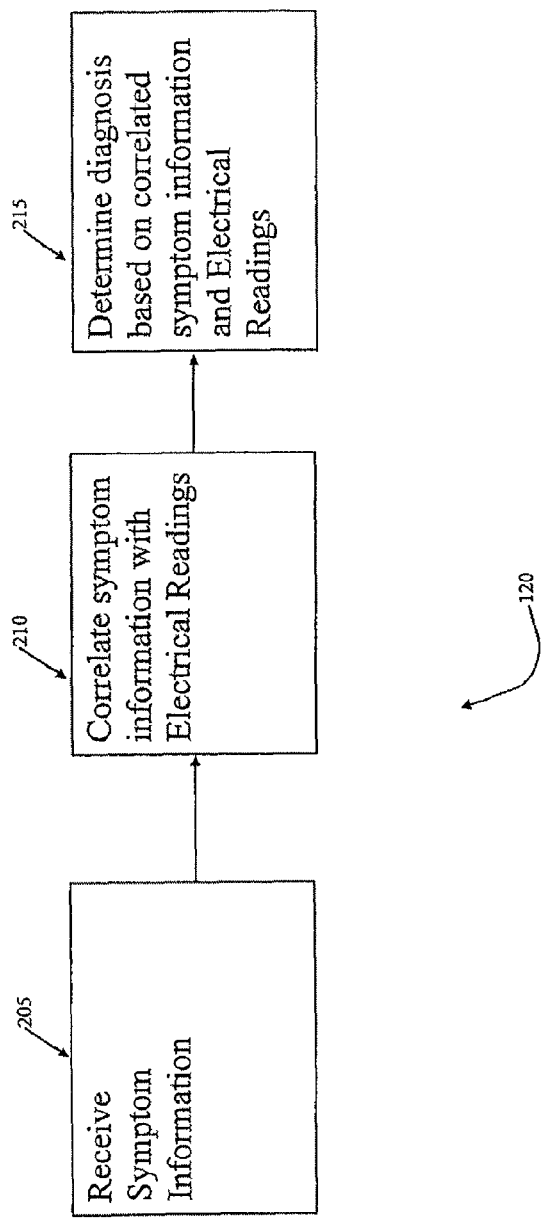
FIG. 2 illustrates a detailed flow chart of one embodiment of the diagnosis phase of the flow chart illustrated in FIG. 1.

Reference is next made to FIG. 2, which illustrates a detailed flow chart of one embodiment of the diagnosis determination, act 120, illustrated in FIG. 1. The system initially receives symptom information from a patient, act 205. Depending on the user interface, the system may prompt a user to select the patient's symptoms or may ask the user a list of predetermined questions designed to elicit the exact symptoms of the patient. The user may be either the patient or some form of facilitator/practitioner. The symptom information may include a wide variety of physical, mental, and emotional symptoms.

The symptom information determined in act 205 is then correlated with the electrical readings determined in act 110. The process of correlation may involve combining certain electrical readings and symptoms that relate to one another. The process of correlation may also involve combining multiple electrical readings that may give a stronger indication of a particular ailment. Various correlation algorithms may be used and remain consistent with the present invention.

The correlated information generated in act 210 is then utilized in determining the diagnosis in act 215. The determination of the diagnosis utilizes the correlated information against known diagnoses to determine the relevant diagnosis of the patient. For example, it may be known that a migraine headache and a skin rash are both indications of an acute food allergy which would then lead to a diagnosis of a food allergy. Various charts or databases of known diagnosis may be utilized to assist in the diagnosis determination from the correlated symptom information and the electrical readings.

Figure 3:
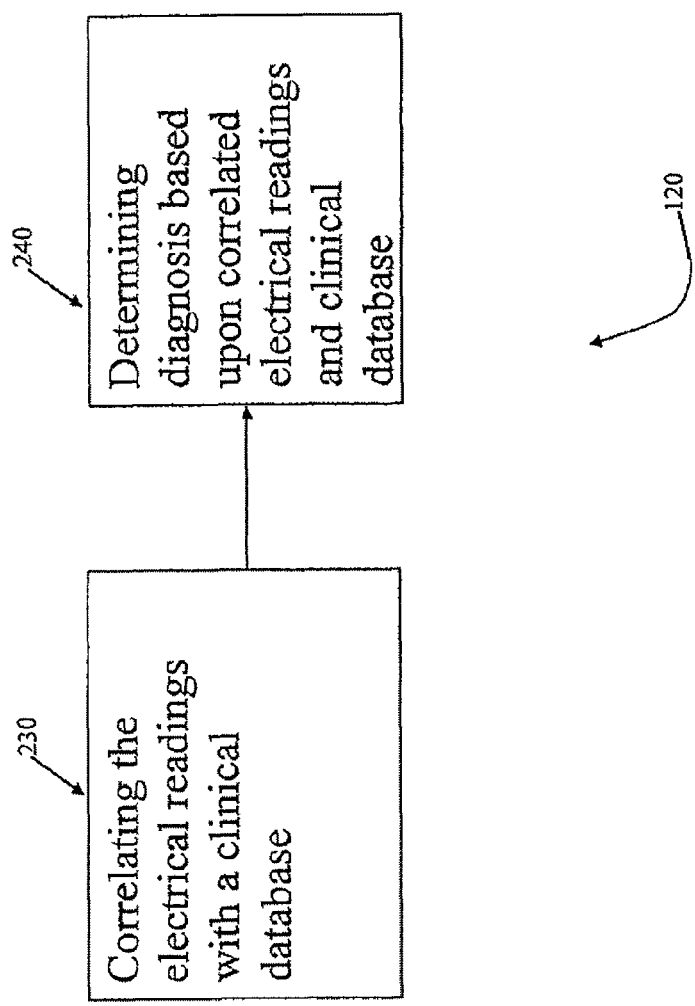
FIG. 3 illustrates a detailed flow chart of an alternative embodiment of the diagnosis phase of the flow chart illustrated in FIG. 1.

Reference is next made to FIG. 3, which illustrated a detailed flow chart of an alternative embodiment of the diagnosis determination, act 120, illustrated in FIG. 1. In this alternative embodiment, the patient's symptoms are never analyzed or recorded. Rather, the electrical readings are correlated with information from a clinical database. The clinical database includes clinical data and is described in more detail with reference to FIG. 4. If the electrical readings of a particular patient in the clinical database are similar to the measured electrical readings, then the appropriate data will be correlated together. Various parameters may be set to determine how close the electrical readings must be in order to be correlated with the measured electrical readings.

The correlated information from act 230 is utilized in determining the diagnosis in act 240. The diagnosis determination may include analyzing the measured electrical readings independently and formulating a diagnosis. This independent diagnosis can then be compared to the diagnosis contained in the correlated clinical data to achieve a more accurate diagnosis. Alternatively, the diagnosis determination could rely solely on the correlated clinical data to determine the diagnosis of the present patient. If multiple patients are identified with similar electrical readings in the clinical database, various filtration techniques could be used to determine which of the diagnoses contained in the correlated clinical information is the most probable diagnosis.

Reference is next made to FIG. 4, which illustrates one embodiment of a clinical database for use with the present invention, designated generally at 400. The clinical database 400 is a database of information that includes electrical readings, symptoms and a diagnosis for each patient. The database may include other information including but not limited to height, weight, and age of the patient. In addition, various types of electrical readings may be included such as impedance readings and square wave response readings. The electrical readings on the clinical database may be taken at specific locations so that they can easily be compared to other patients. For example, reading 1 may be a right palm acupuncture point reading.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A method for determining appropriate treatments based on electrical readings, comprising:
   measuring at least two measured electrical readings from acupuncture points on a human body;
   accessing a clinical information database containing a plurality of patient listings of individual patient data, each patient listing comprising:
      at least two patient electrical readings from acupuncture points of an individual patient; and
      a known diagnosis of a patient ailment for that patient, the known diagnosis being associated with the at least two patient electrical readings;
   automatically using a correlation algorithm to generate a matching diagnosis of a particular ailment by searching the clinical information database for patient listings having patient electrical readings similar to the at least two measured electrical readings and selecting the associated known diagnosis of one of the patient listings having patient electrical readings similar to the measured electrical readings; and
   determining treatment information by correlating the matching diagnosis to a set of known treatment information corresponding to the matching diagnosis.

2. The method of claim 1, wherein measuring at least two measured electrical readings further includes measuring an impedance from a particular location on the human body to a second location on the human body.

3. The method of claim 1, wherein measuring at least two measured electrical readings further includes measuring a resistance from a particular location on the human body to a second location on the human body.

4. The method of claim 1, wherein each patient listing further comprises patient symptom information and wherein automatically using a correlation algorithm to generate the matching diagnosis of the particular ailment further includes:
   receiving input symptom information;
   searching the clinical information database for patient listings having patient symptom information similar to the input symptom information in addition to the similar at least two electrical readings; and
   generating diagnosis information based on the known diagnosis of the patient ailment of the associated patient listing.

5. The method of claim 4, wherein receiving input symptom information comprises at least one of:
   prompting a user to select symptoms; and
   providing a set of predetermined questions designed to elicit exact symptom information.

6. The method of claim 1, wherein the known diagnosis of the patient ailment for each of the patient listings includes homeopathic ailments.

7. The method of claim 1, wherein the known diagnosis of the patient ailment for each of the patient listings includes medical ailments and conditions.

8. The method of claim 1, wherein the known diagnosis of the patient ailment for each of the patient listings includes chiropractic conditions.

9. The method of claim 1, wherein determining treatment information by correlating the matching diagnosis to the set of known treatment information corresponding to the matching diagnosis includes assigning treatment information based solely upon the matching diagnosis.

10. The method of claim 1, wherein determining treatment information by correlating the matching diagnosis to the set of known treatment information corresponding to the matching diagnosis includes assigning treatment information based upon known treatments for the matching diagnosis.

11. The method of claim 1, wherein determining treatment information by correlating the matching diagnosis to the set of known treatment information corresponding to the matching diagnosis includes assigning treatment information based upon homeopathic recommended treatments for the matching diagnosis.

12. The method of claim 1, wherein determining treatment information by correlating the matching diagnosis to the set of known treatment information corresponding to the matching diagnosis includes assigning treatment information based upon medically recommended treatments for the matching diagnosis.

13. The method of claim 1, wherein measuring at least two measured electrical readings comprises measuring a square wave response at the acupuncture points.

14. The method of claim 1, wherein measuring at least two measured electrical readings comprises measuring a rectifying response at the acupuncture points.

15. The method of claim 1, wherein measuring at least two measured electrical readings comprises measuring a frequency filtration response at the acupuncture points.

16. A method for determining a diagnosis of a particular ailment and a treatment thereof from electrical readings, comprising:
   measuring at least two measured electrical readings from meridian points for different regions of a human body;
   accessing a clinical information database containing a plurality of patient listings of individual patient data, each patient listing comprising:
      at least two patient electrical readings from acupuncture points of an individual patient; and
      a known diagnosis of a patient ailment for that patient, the known diagnosis being associated with the at least two patient electrical readings;
   automatically using a correlation algorithm to generate a matching diagnosis of the particular ailment by searching the clinical information database for patient listings having patient electrical readings similar to the at least two measured electrical readings and selecting the associated known diagnosis of one of the patient listings having patient electrical readings similar to the measured electrical readings; and
   determining treatment information by correlating the matching diagnosis to a set of known treatment information corresponding to the matching diagnosis.

17. The method of claim 16, wherein measuring at least two measured electrical readings further includes measuring an impedance from a particular location on the human body to a second location on the human body.

18. The method of claim 16, wherein measuring at least two measured electrical readings further includes measuring a resistance from a particular location on the human body to a second location on the human body.

19. The method of claim 16, wherein the at least two measured electrical readings include a plurality of electrical readings corresponding to acupuncture points on the human body.

20. The method of claim 16 wherein each patient listing further comprises patient symptom information and wherein automatically using a correlation algorithm to generate a matching diagnosis of the particular ailment by correlating at least two electrical readings further includes:
   receiving input symptom information;
   searching the clinical information database for patient listings having patient symptom information similar to the input symptom information in addition to the at least two similar electrical readings; and
   generating diagnosis information based on the known diagnosis of the patient ailment of the associated patient listing.

21. The method of claim 20 wherein receiving input symptom information comprises at least one of:
   prompting a user to select symptoms; and
   providing a set of predetermined questions designed to elicit exact symptom information.

22. The method of claim 16, wherein the known diagnosis of the patient ailment for each of the patient listings includes homeopathic ailments.

23. The method of claim 16, wherein the known diagnosis of the patient ailment for each of the patient listings includes medical ailments and conditions.

24. The method of claim 16, wherein the known diagnosis of the patient ailment for each of the patient listings includes chiropractic conditions.

25. The method of claim 16, wherein determining treatment information by correlating the matching diagnosis to the set of known treatment information includes assigning treatment information based solely upon the matching diagnosis.

26. The method of claim 16, wherein determining treatment information by correlating the matching diagnosis to the set of known treatment information includes assigning treatment information based upon known treatments for the matching diagnosis.

27. The method of claim 16, wherein determining treatment information by correlating the matching diagnosis to the set of known treatment information includes assigning treatment information based upon homeopathic recommended treatments for the matching diagnosis.

28. The method of claim 16, wherein determining treatment information by correlating the matching diagnosis to the set of known treatment information includes assigning treatment information based upon medically recommended treatments for the matching diagnosis.

29. The method of claim 16, wherein measuring at least two measured electrical readings comprises measuring a square wave response at the meridian points.

30. The method of claim 16, wherein measuring at least two measured electrical readings comprises measuring a rectifying response at the meridian points.

31. The method of claim 6, wherein measuring at least two measured electrical readings comprises measuring a frequency filtration response at the meridian points.

\* \* \* \* \*